US012593878B2

(12) United States Patent　　(10) Patent No.:　US 12,593,878 B2

Washington　　(45) Date of Patent:　Apr. 7, 2026

(54) ABSORBENT UNDERGARMENT SYSTEM

(71) Applicant: Dana' Washington, Austin, TX (US)

(72) Inventor: Dana' Washington, Austin, TX (US)

( * ) Notice: Subject to any disclaimer, the term of this patent is extended or adjusted under 35 U.S.C. 154(b) by 554 days.

(21) Appl. No.: 18/076,611

(22) Filed: Dec. 7, 2022

(65) Prior Publication Data

US 2024/0188645 A1　Jun. 13, 2024

(51) Int. Cl.
| | |
|---|---|
| *A61F 13/15* | (2006.01) |
| *A41B 9/00* | (2006.01) |
| *A61F 13/49* | (2006.01) |
| *A61F 13/496* | (2006.01) |
| *A61F 13/505* | (2006.01) |

(52) U.S. Cl.
CPC ........ *A41B 9/001* (2013.01); *A61F 13/49006* (2013.01); *A61F 13/496* (2013.01); *A61F 13/505* (2013.01)

(58) Field of Classification Search
CPC .. A41B 9/001; A61F 13/49006; A61F 13/496; A61F 13/505; A61F 13/5055
USPC ...................... 2/400, 222.78, 1, 73; 604/396
See application file for complete search history.

(56) References Cited

U.S. PATENT DOCUMENTS

| | | | |
|---|---|---|---|
| 5,032,119 | A | 7/1991 | Hookano |
| 7,384,415 | B2 | 6/2008 | Kline et al. |
| 9,198,807 | B2 | 12/2015 | Evenson et al. |
| 9,301,886 | B2 | 4/2016 | Fernández |

| | | | |
|---|---|---|---|
| 10,667,964 | B2 | 6/2020 | Sierra |
| 2006/0224136 | A1 | 10/2006 | Martinez |
| 2007/0083181 | A1* | 4/2007 | LaVon ................. A61F 13/532 |
| | | | 604/385.19 |

(Continued)

FOREIGN PATENT DOCUMENTS

| | | |
|---|---|---|
| KR | 20000035202 A | 11/2006 |
| KR | 200463267 Y1 | 10/2012 |
| KR | 101676058 B1 | 11/2016 |

OTHER PUBLICATIONS

Etsy, "Reusable Panty Liners, Light Bladder Leakage, Cloth Pads, Eco-Friendly Period Products, Mini Liner, Regular Liner, Maxi Liner," accessed May 2022, https://www.etsy.com/listing/976626206/reusable-menstrual-liners-period-pads?msclkid=059133e4d0ad11ec909f85a0dc37c248, 20 pages.

(Continued)

*Primary Examiner* — Jacqueline F Stephens

(74) *Attorney, Agent, or Firm* — Pillsbury Winthrop Shaw Pittman LLP

(57)　　　ABSTRACT

Provided is an undergarment system that includes undergarment body portion having a first edge and a second edge opposite the undergarment body portion from the first edge. The undergarment body portion defines a pocket aperture and an undergarment body portion cavity. The undergarment system also includes a first edge member extending from the first edge, a second edge member extending from the first edge, a third edge member extending from the second edge, and a fourth edge member extending from the second edge. The undergarment body portion, the first edge member, the second edge member, the third edge member, and the fourth edge member are configured to form a waist aperture, a first leg aperture, and a second leg aperture when the first edge member is secured to the second edge member and the third edge member is secured to the fourth edge member.

20 Claims, 13 Drawing Sheets

(56)            References Cited

U.S. PATENT DOCUMENTS

| 2012/0220976 | A1 | 8/2012 | Morse et al. |
| 2016/0030255 | A1 | 2/2016 | Rescorl et al. |
| 2016/0262960 | A1 | 9/2016 | Sierra |

OTHER PUBLICATIONS

Web Archive of Treehugger.com, The 8 Best Reusable Menstrual Pads of 2022, Apr. 25, 2022, http://web.archive.org/web/20220425034153/https://www.treehugger.com/best-reusable-menstrual-pads-5116284, 25 pages.

* cited by examiner

400

Provide an undergarment system — 402

Couple a first absorbent pad to the undergarment system — 404

Couple a second absorbent pad to the undergarment system — 406

Couple edge member securing elements together to form a first leg aperture, a second leg aperture, and a waist aperture — 408

Disassemble the undergarment system — 410

ABSORBENT UNDERGARMENT SYSTEM

BACKGROUND

1. Field

The present disclosure relates generally to undergarments and more particularly to an absorbent undergarment.

2. Description of the Related Art

Undergarments are clothing worn beneath outer clothes. Undergarments serve to keep outer garments from being soiled from bodily excretions, provide support, to lessen the friction of outerwear against the skin, to shape the body, to provide concealment for parts of the body or other uses. In cold weather, undergarments are sometimes worn to provide additional warmth. Special types of undergarments have religious significance. Some items of clothing are designed as undergarments, while others, such as T-shirts and certain types of shorts, are appropriate both as undergarments and as outer clothing. If made of suitable material some or textile, undergarments can serve as nightwear or swimsuits, and some are intended for visual appeal.

3. SUMMARY

The following is a non-exhaustive listing of some aspects of the present techniques. These and other aspects are described in the following disclosure.

Some aspects include an undergarment system, comprising: an undergarment body portion having a first edge and a second edge opposite the undergarment body portion from the first edge, wherein the undergarment body portion defines a pocket aperture and an undergarment body portion cavity; a first edge member extending from the first edge; a second edge member extending from the first edge; a third edge member extending from the second edge; and a fourth edge member extending from the second edge, wherein the undergarment body portion, the first edge member, the second edge member, the third edge member, and the fourth edge member are configured to form a waist aperture, a first leg aperture, and a second leg aperture when the first edge member is secured to the second edge member and the third edge member is secured to the fourth edge member.

Some aspects include method, including: providing an undergarment system that includes an undergarment body portion having a first edge and a second edge opposite the undergarment body portion from the first edge, wherein the undergarment body portion defines a pocket aperture and an undergarment body portion cavity; a first edge member extending from the first edge; a second edge member extending from the first edge; a third edge member extending from the second edge; and a fourth edge member extending from the second edge; coupling a first absorbent pad to the undergarment body portion by inserting the first absorbent pad into the undergarment body portion cavity; and coupling a second absorbent pad to the undergarment body portion via an undergarment connector provided on the second absorbent pad

4. BRIEF DESCRIPTION OF THE DRAWINGS

The above-mentioned aspects and other aspects of the present techniques will be better understood when the present application is read in view of the following FIGS. in which like numbers indicate similar or identical elements:

Figure 1A:
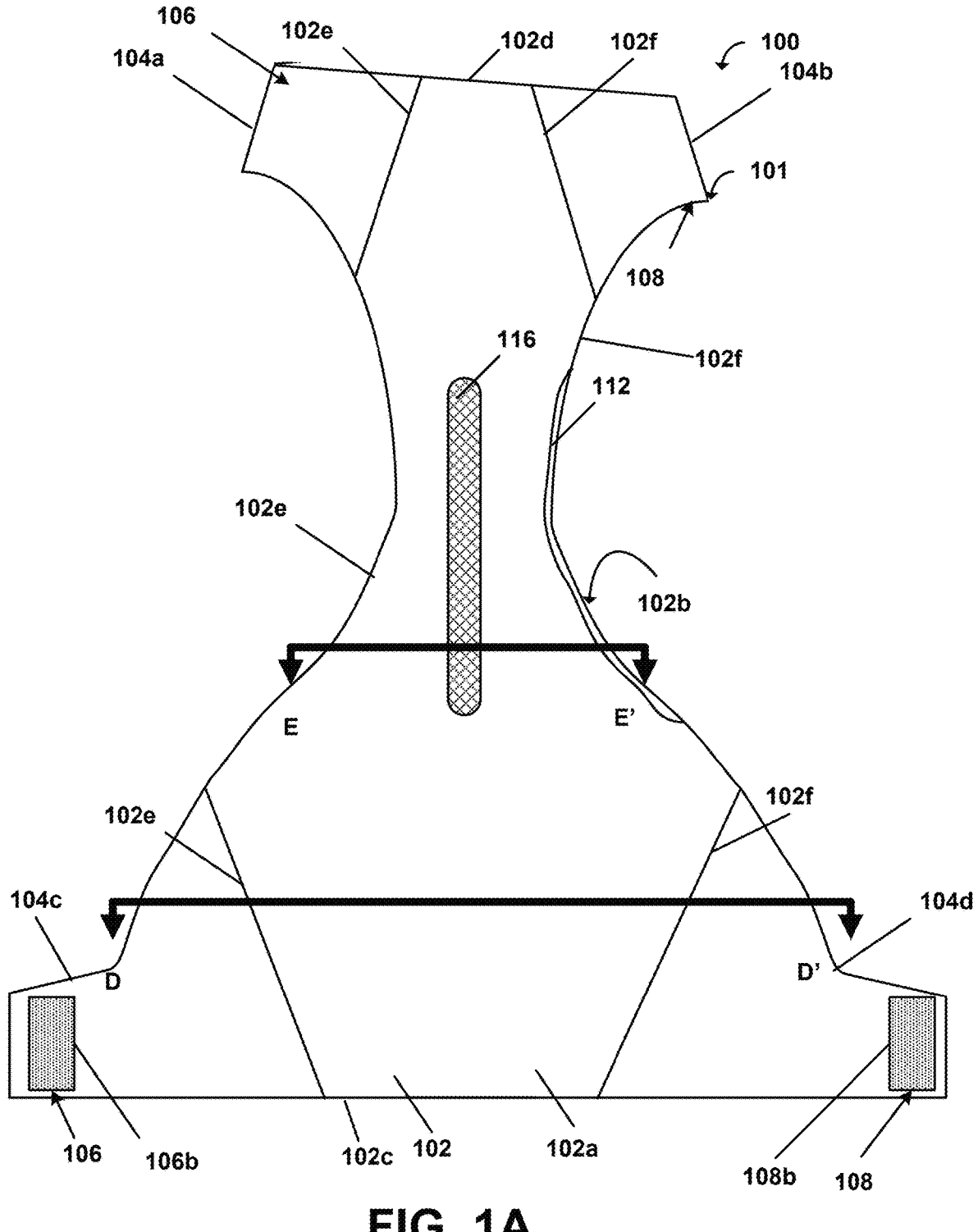
FIG. 1A illustrates an interior view of an undergarment system, in accordance with some embodiments of the present disclosure.
Figure 1B:
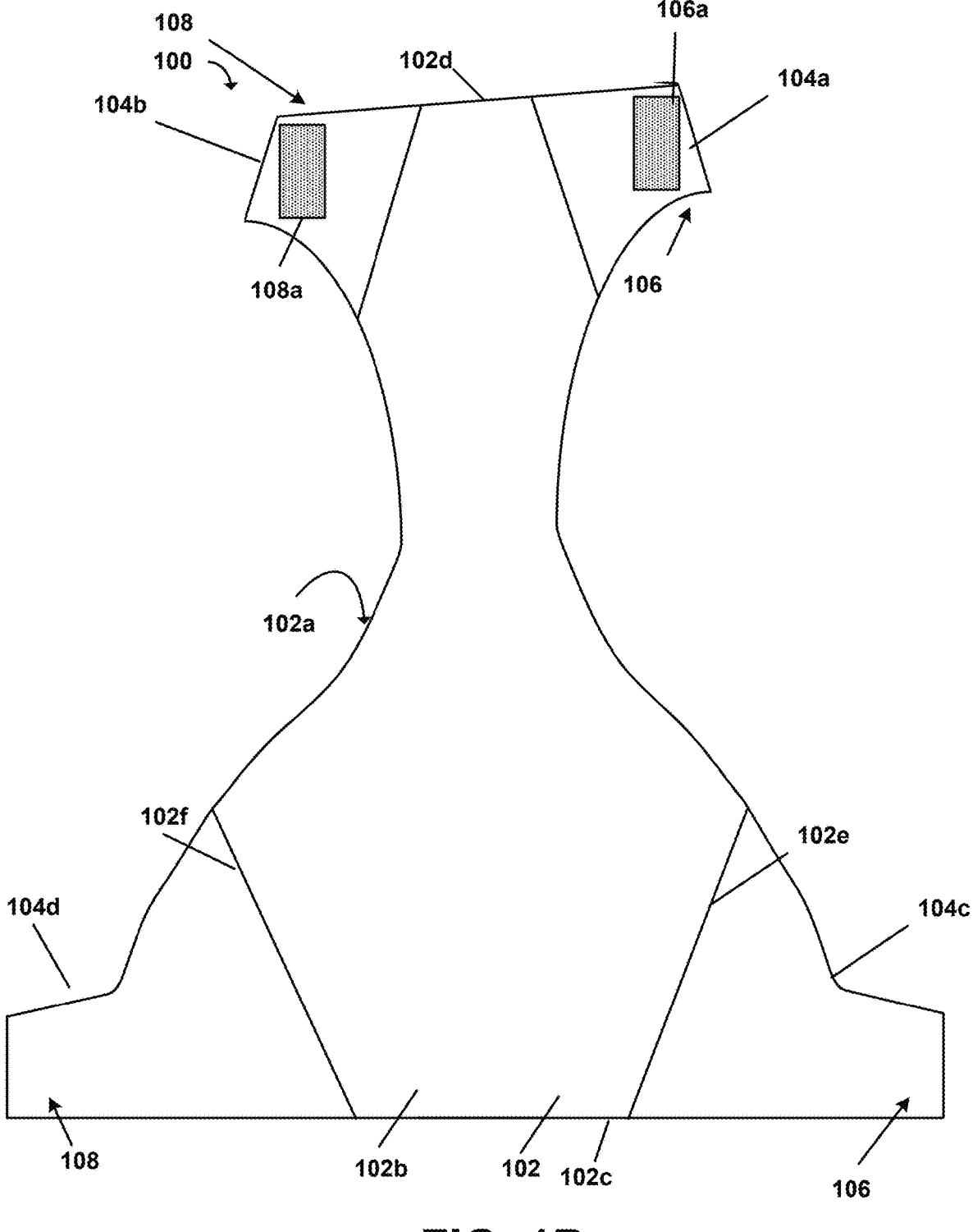
FIG. 1B illustrates an exterior view of the undergarment system of FIG. 1A, in accordance with some embodiments of the present disclosure.
Figure 1C:
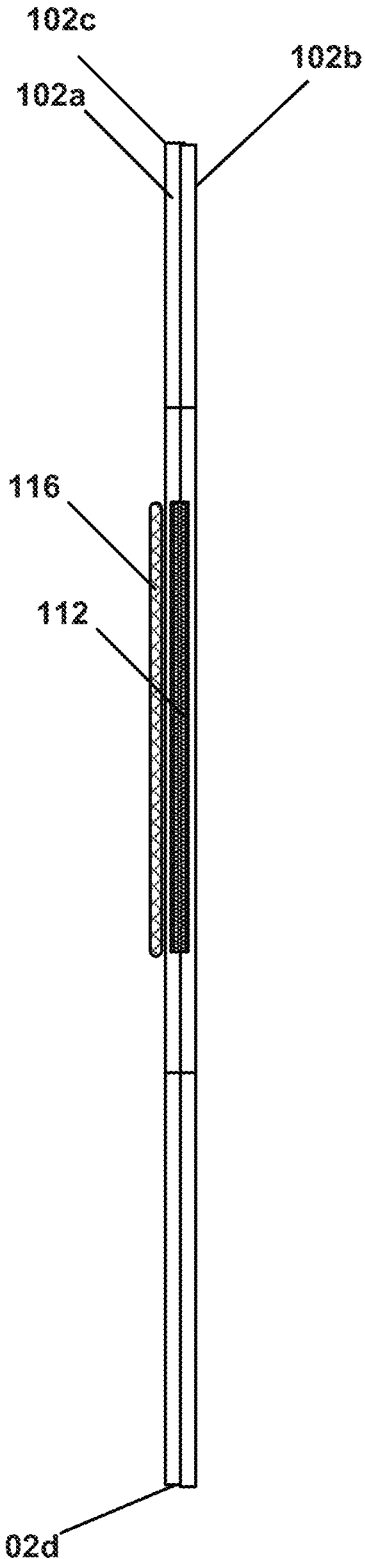
FIG. 1C illustrates a side view of the undergarment system of FIGS. 1A-1B, in accordance with some embodiments of the present disclosure.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventor had to both invent solutions and, in some cases just as importantly, recognize problems overlooked (or not yet foreseen) by others in the field of undergarments. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

As described above, undergarments are ubiquitous and serve one or more different functions such as protecting outer garments from bodily excretions. One common bodily excretion is blood and mucosal tissue discharged during the female menstrual cycle. Sanitary napkins, tampons, and menstrual cups are often used to collect or absorb menstrual excretions. However, these devices are often uncomfortable and generate a lot of waste, which ends up in landfills or causes problems with sewage systems. Alternatives to these disposable devices, include reusable cloth pads that may be inserted between the undergarment and the user. Also, as discussed above, undergarments may have extra liners sewn into the undergarment to help absorb fluids. However, these undergarments are often bulky such that it is noticeable to a wearer or observer, or the undergarment is not absorbable enough. Due to the unpredictable nature of menstrual flows, it is sometimes difficult for a user to know how much absorption is needed. Other drawbacks with current undergarments are that menstrual undergarments are used primarily during the menstrual cycle. In other words, the user likely does not wear them during other times when the menstrual cycle is not occurring. Also, once soiled, current menstrual undergarments are difficult to take off without soiling the user and outer clothing.

The systems and methods of the present disclosure provide a solution to these problems by providing an absorbent undergarment system. The undergarment system may include a removable absorbent pad that may extend up the front and back of an undergarment body portion to a waistband. In other embodiments, the undergarment or an absorbent pad coupled to the undergarment may include a unique layering of cloth material to provide absorption but is comfortable to the user or maintains a low profile. In other embodiments, undergarment edge member securing elements may be provided that allow the user to attach and detach the undergarment at the pelvic region rather than requiring the user to wear or remove the undergarment via the user's legs. A variety of undergarment edge member securing elements are contemplated to secure the undergarment system to the user for use but allow the user to decouple the undergarment edge member securing elements for removal of the undergarment system from the user. In yet other embodiments, the undergarment body portion may define a cavity in which the absorbent pad may be inserted, or which may receive a second absorbent pad. In other embodiments, the absorbent pad may include an undergarment connector that connects the absorbent pad to the undergarment.

Referring now to FIGS. 1A, 1B, 1C, 1D, and 1E, an embodiment of an undergarment system 100 is illustrated. In an embodiment, the undergarment system 100 may provide an undergarment 101 such as, for example, a panty, a brief, a boxer short, lingerie, a compression short, a thong, a bikini, a boyshort, a hipster, a hi-waist, a boxer brief, or any other undergarment that would be apparent to one of skill in the art in possession of the present disclosure. The undergarment system 100 may include an undergarment body portion 102. The undergarment body portion 102 may include an undergarment body portion interior face 102a, an undergarment body portion exterior face 102b that is located opposite the undergarment body portion 102 from the undergarment body portion interior face 102a, and at least one wall extending between the undergarment body portion interior face 102a and the undergarment body portion exterior face 102b. The undergarment body portion 102 may also include an undergarment body portion waist edge 102c extending between the undergarment body portion interior face 102a and the undergarment body portion exterior face 102b, an undergarment body portion waist edge 102d located opposite the undergarment body portion 102 from the undergarment body portion waist edge 102c and extending between the undergarment body portion interior face 102a and the undergarment body portion exterior face 102b, and a pair of undergarment body portion leg edges 102e and 102f that are located opposite each other on the undergarment body portion 102 and that each extend between the undergarment body portion interior face 102a, the undergarment body portion exterior face 102b, the undergarment body portion waist edge 102c, and the undergarment body portion waist edge 102d. In the illustrated embodiment, the undergarment body portion 102 may be configured in an hourglass shape. However, in other embodiments the undergarment body portion 102 may be configured in an oval shape, a rectangular shape, a triangular shape, or any other shape that would be apparent to one of skill in the art in possession of the present disclosure that can provide adequate coverage of the female genitalia.

In various embodiments, the undergarment 101 may include an edge member 104a that extends from the undergarment body portion leg edge 102e and that is adjacent the undergarment body portion waist edge 102d. The undergarment 101 may include an edge member 104b that extends from the undergarment body portion leg edge 102f and that is adjacent the undergarment body portion waist edge 102d. Furthermore, the undergarment 101 may include an edge member 104c that extends from the undergarment body portion leg edge 102e and that is adjacent the undergarment body portion waist edge 102c. In addition, the undergarment 101 may include an edge member 104d that extends from the undergarment body portion leg edge 102*f* and that is adjacent the undergarment body portion waist edge 102*c*. In various embodiments, the undergarment body portion 102 includes a first liquid absorbent capacity that is greater than a second liquid absorbent capacity than at least one of the edge member 104*a*, the edge member 104*b*, the edge member 104*c*, or the edge member 104*d*. Edge members 104*a*, 104*b*, 104*c*, and 104*d* correspond respectively to a first edge member, a second edge member, a third edge member, and a fourth edge member.

In various embodiments, the edge member 104*a* and the edge member 104*c* may include an edge member securing element 106. The edge member 104*a* may include an edge member securing sub-element 106*a* of the edge member securing element 106 and the edge member 104*c* may include an edge member securing sub-element 106*b* of the edge member securing element 106 that is configured to form a detachable coupling with the edge member securing sub-element 106*a*. Similarly, the edge member 104*b* and the edge member 104*d* may include an edge member securing element 108. The edge member 104*b* may include an edge member securing sub-element 108*a* of the edge member securing element 108 and the edge member 104*d* may include an edge member securing sub-element 108*b* of the edge member securing element 108 that is configured to form a detachable coupling with the edge member securing sub-element 108*a*. For example, the edge member securing elements 106 and 108 may include a hook-and-loop system, a button system, an extender hook system, a strap hook system, or any other fastener system that would be apparent to one of skill in the art in possession of the present disclosure. When the edge member securing sub-element 106*a* is coupled to the edge member securing sub-element 106*b*, the edge member 104*a*, the edge member 104*c*, and the undergarment body portion 102 may form a first leg aperture. Similarly, when the edge member securing sub-element 108*a* is coupled to the edge member securing sub-element 108*b*, the edge member 104*b*, the edge member 104*d*, and the undergarment body portion 102 may form a second leg aperture. When the edge member securing sub-element 106*a* is coupled to the edge member securing sub-element 106*b* and when the edge member securing sub-element 108*a* is coupled to the edge member securing sub-element 108*b*, the edge member 104*a*, the edge member 104*b*, the edge member 104*c*, the edge member 104*d* and the undergarment body portion 102 may form the first leg aperture, the second leg aperture, and a waist aperture.

Figures 1D, 1E:
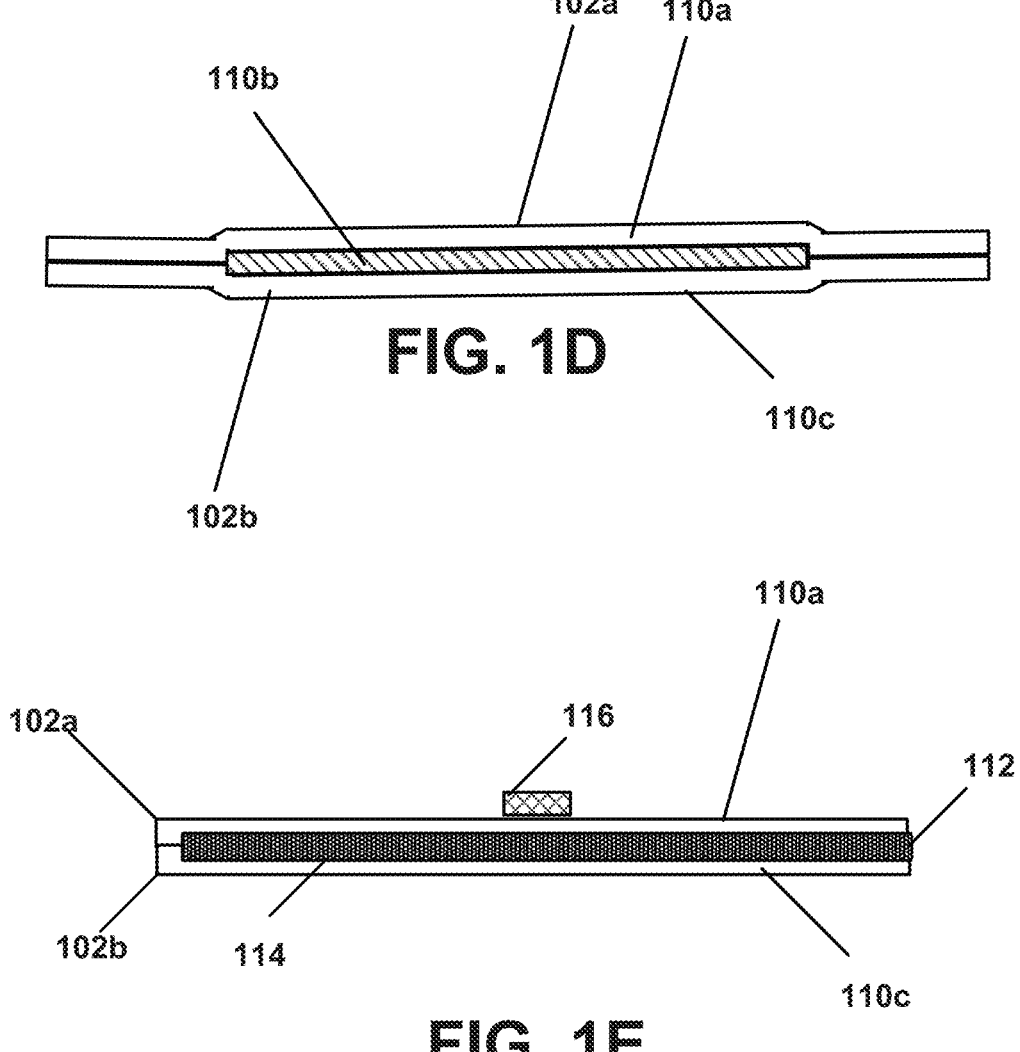
FIG. 1D illustrates a cross-sectional view of the undergarment system of FIG. 1A along the cutting plane DD' of FIG. 1A, in accordance with some embodiments of the present disclosure.
FIG. 1E illustrates a cross-sectional view of the undergarment system of FIG. 1A along the cutting plane EE' of FIG. 1A, in accordance with some embodiments of the present disclosure.

In various embodiments, the undergarment body portion 102 may include one or more layers. For example, the undergarment body portion 102 may include a single layer that provides the undergarment body portion interior face 102*a* and the undergarment body portion exterior face 102*b*. As illustrated in FIG. 1D, the undergarment body portion 102 may include a layer 110*a* that provides the undergarment body portion interior face 102*a*, a layer 110*b* that is adjacent to the layer 110*a*, and a layer 110*c* that is adjacent to the layer 110*b*, and opposite the undergarment body portion 102 from layer 110*a*. The layer 110*c* may provide the undergarment body portion exterior face 102*b*. The layers 110*a* or 110*c* may include a cotton material or a bamboo material. The layer 110*b* may include a bamboo material, a thermoplastic polyurethane material, or a microfiber material.

Figure 2A:
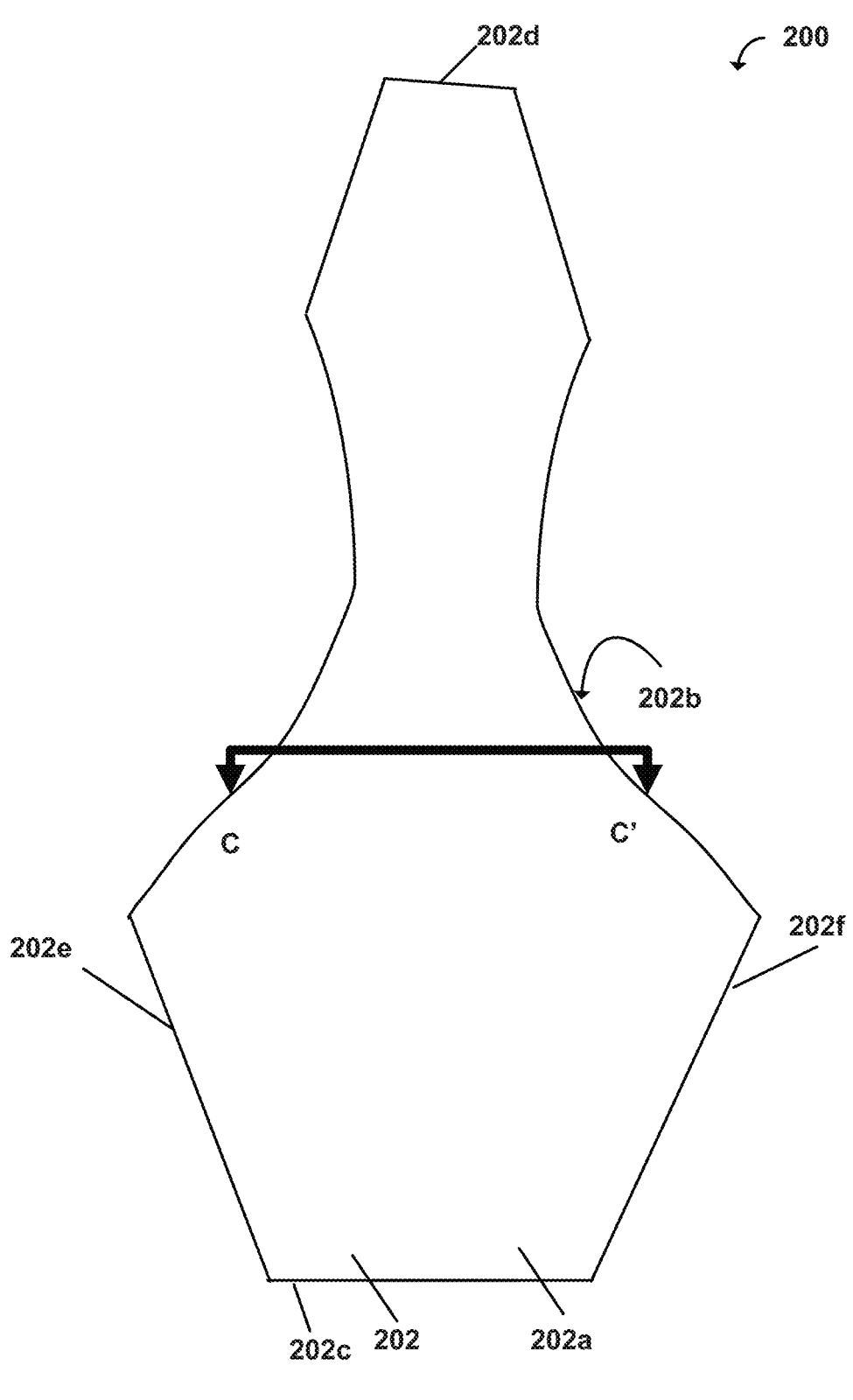
FIG. 2A illustrates an interior view of an absorbent pad, in accordance with some embodiments of the present disclosure.
Figures 2B, 2C:
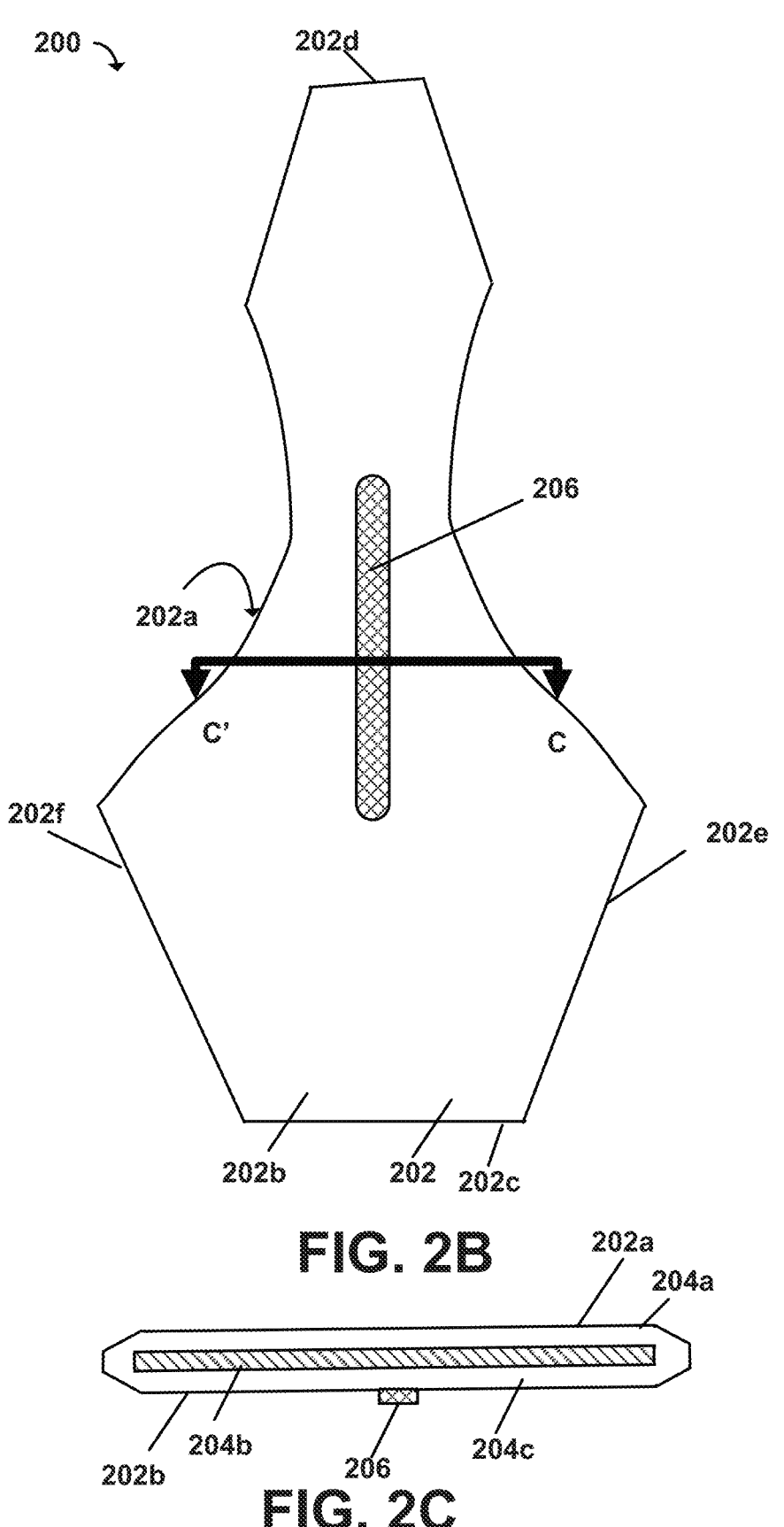
FIG. 2B illustrates an exterior view of the absorbent pad of FIG. 2A, in accordance with some embodiments of the present disclosure.
FIG. 2C illustrates a cross-sectional view of the absorbent pad of FIG. 2A along the cutting plane CC' of FIG. 2A, in accordance with some embodiments of the present disclosure.

In some embodiments, as illustrated in FIG. 1E, the undergarment body portion 102 may include the layer 110*a* and the layer 110*c* such that the layer 110*a* and 110*c* define a pocket aperture 112 that provides access to an undergarment body portion cavity 114 configured to house an absorbent pad (e.g., an absorbent pad 200 of FIGS. 2A-2C). The pocket aperture 112 may be defined on one or more of the undergarment body portion interior face 102*a*, the undergarment body portion exterior face 102*b*, the undergarment body portion waist edge 102*c*, the undergarment body portion waist edge 102*d*, the undergarment body portion leg edge 102*e*, or the undergarment body portion leg edge 102*f*. In various embodiments, the layers 110*a* and 110*c* may include a pocket aperture closure device such as buttons, a zipper, hook and loop fastener or other fasteners to close the pocket aperture 112 when an absorbent pad is inserted into the undergarment body portion cavity 114. The aperture closure device may be configured such that the user can undo the aperture closure device to access the pocket aperture 112 to remove the absorbent pad.

In some embodiments, in addition to or alternatively to the pocket aperture 112, the undergarment body portion 102 may include an absorbent pad connector 116. The absorbent pad connector 116 may be configured to couple the absorbent pad (e.g., absorbent pad 200) to the undergarment body portion 102. For example, the absorbent pad connector 116 may include a hook-and-loop system, a button system, an adhesive system, a magnetic fastener system (e.g., thin magnetic disks positioned along the undergarment body portion waist edges 102*c* and 102*d* and the undergarment body portion leg edges 102*e* and 102*f*) or any other fastener that would be apparent to one of skill in the art in possession of the present disclosure. As such, the undergarment system 100 may be configured with one or more absorbent pads (e.g., one via the pocket aperture 112 or one via the absorbent pad connector 116). By providing multiple location through which one or more absorbent pads can couple to the undergarment system 100, the undergarment system 100 may provide the user options for protection and comfort based on the level of absorbency or comfort that the user needs for a particular time. While a specific example of the undergarment system 100 is illustrated in FIGS. 1A-1E, one of skill in the art in possession of the present disclosure will recognize that other variations and embodiments may be contemplated and fall under the scope of the present disclosure as well.

Referring now to FIGS. 2A, 2B and 2C, an embodiment of an absorbent pad 200 is illustrated that is discussed above as being insertable or coupled to the undergarment body portion 102 of FIGS. 1A-1E. The absorbent pad 200 may include an absorbent pad body portion 202. The absorbent pad body portion 202 may include an absorbent pad body portion interior face 202*a*, an absorbent pad body portion exterior face 202*b* that is located opposite the absorbent pad body portion 202 from the absorbent pad body portion interior face 202*a*, and at least one wall extending between the absorbent pad body portion interior face 202*a* and the absorbent pad body portion exterior face 202*b*. For example, the absorbent pad body portion 202 may include an absorbent pad body portion waist edge 202*c* extending between the absorbent pad body portion interior face 202*a* and the absorbent pad body portion exterior face 202*b*, an absorbent pad body portion waist edge 202*d* located opposite the absorbent pad body portion 202 from the absorbent pad body portion waist edge 202*c* and extending between the absorbent pad body portion interior face 202*a* and the absorbent pad body portion exterior face 202*b*, and a pair of absorbent pad body portion leg edges 202*e* and 202*f* that are located opposite each other on the absorbent pad body portion 202 and that each extend between the absorbent pad body portion interior face 202*a*, the absorbent pad body portion exterior face 202*b*, the absorbent pad body portion waist edge 202*c*, and the absorbent pad body portion waist edge 202*d*. In the illustrated embodiment the absorbent pad body portion 202 may be configured in an hourglass shape, an oval shape, a rectangular shape, a triangular shape, or any other shape that would be apparent to one of skill in the art in possession of the present disclosure that can provide adequate coverage or at least a portion of the female genitalia.

In various embodiments, the absorbent pad 200 may include one or more layers. For example, the absorbent pad 200 may include a single layer that provides the absorbent pad body portion interior face 202*a* and the absorbent pad body portion exterior face 202*b*. As illustrated in FIG. 2C, the absorbent pad 200 may include a layer 204*a* that provides the absorbent pad body portion interior face 202*a*, a layer 204*b* that is adjacent to the layer 204*a*, and a layer 204*c* that is adjacent to the layer 204*b*, and opposite the absorbent pad 200 from layer 204*a*. The layer 204*c* may provide the absorbent pad body portion exterior face 202*b*.

In some embodiments, absorbent pad 200 may include an undergarment connector 206 that may be configured to couple with the corresponding absorbent pad connector 116 of FIGS. 1A-1E. The undergarment connector 206 may be configured to couple the absorbent pad 200 to the undergarment body portion 102 via the absorbent pad connector 116. For example, the undergarment connector 206 may include a hook-and-loop system, a button system, an adhesive system, a magnetic fastener system (e.g., thin magnetic disks positioned along the absorbent pad body portion waist edges 202*c* and 202*d* and the absorbent pad body portion leg edges 202*e* and 202*f*), or any other fastener that would be apparent to one of skill in the art in possession of the present disclosure. While the undergarment connector 206 is illustrated as being central to the absorbent pad 200, in various embodiments, the undergarment connector 206 may be located along one or more of the edges 202*c*-202*f* on the absorbent pad body portion interior face 202*a* such that absorbent pad 200 can more securely couple to the undergarment body portion 102. Similarly, in other embodiments, the undergarment connector 206 may be configured to couple the absorbent pad 200 to the undergarment body portion 102 or the undergarment system 100 without corresponding connectors on the undergarment body portion 102 or the undergarment system 100. For example, the absorbent pad 200 may include connector wings that extend from the edges 202*e* and 202*f* that are configured to wrap around the undergarment body portion 102 and connect to each other forming an aperture that the undergarment body portion 102 is provided through. In yet other embodiments, the absorbent pad 200 may be configured to be insertable into the undergarment body portion cavity 114 defined by the undergarment body portion 102 via the undergarment body portion cavity 114. While a specific example of the absorbent pad 200 is illustrated in FIGS. 2A-2C, one of skill in the art in possession of the present disclosure will recognize that other variations and embodiments may be contemplated and fall under the scope of the present disclosure as well.

Figure 3C:
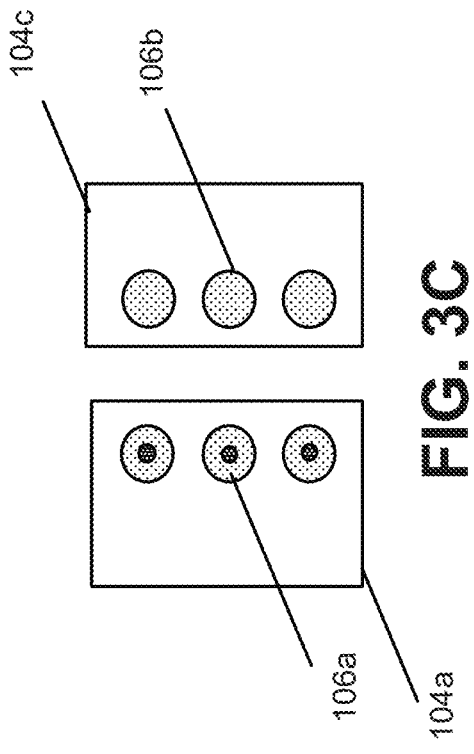
FIG. 3C illustrates an embodiment of an edge member securing element included on the undergarment system of FIGS. 1A-1E, in accordance with some embodiments of the present disclosure.
Figure 3D:
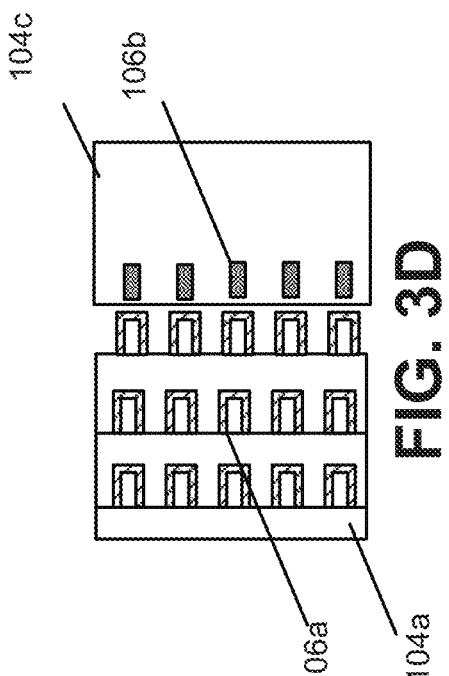
FIG. 3D illustrates an embodiment of an edge member securing element included on the undergarment system of FIGS. 1A-1E, in accordance with some embodiments of the present disclosure.
Figure 3A:
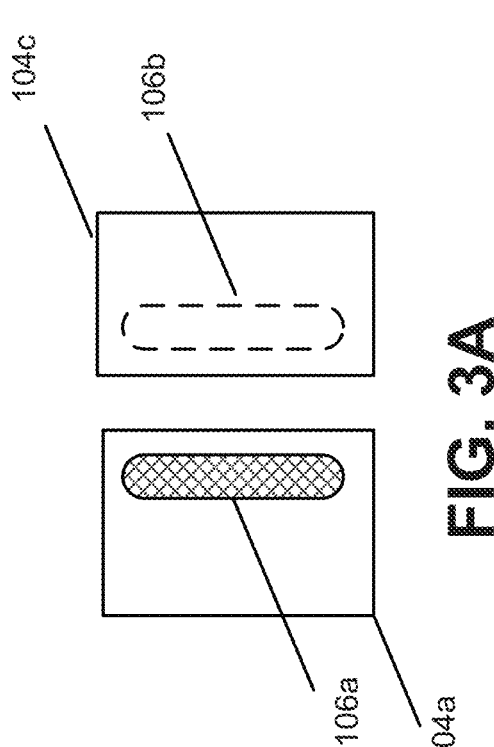
FIG. 3A illustrates an embodiment of an edge member securing element included on the undergarment system of FIGS. 1A-1E, in accordance with some embodiments of the present disclosure.
Figure 3B:
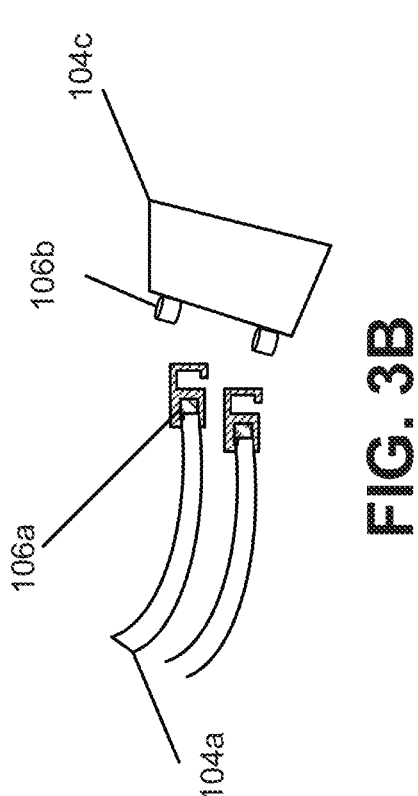
FIG. 3B illustrates an embodiment of an edge member securing element included on the undergarment system of FIGS. 1A-1E, in accordance with some embodiments of the present disclosure.

FIGS. 3A-3D illustrate various embodiments of edge members (e.g., edge members 104*a*-104*d*), edge member securing elements (e.g., edge member securing elements 106 and 108) with their edge member securing sub-elements (e.g., edge member securing sub-elements 106*a*, 106*b*, 108*a*, and 108*b*). For example, FIG. 3A illustrates edge members 104*a* and 104*c* (edge members 104*b* and 104*d* as well). The edge member securing element 106 (but could be edge member securing elements 108) may include a hook and loop system having an edge member securing sub-element 106*a* including the hook portion or the loop portion and the edge member securing sub-element 106*b* including the corresponding loop portion or the hook portion. FIG. 3B illustrates another embodiment where the edge member securing element 106 provided by the edge members 104*a* and 104*c* includes a strap hook system. The edge member securing sub-element 106*a* may include one or more hooks and the edge member securing sub-element 106*b* may include one or more corresponding straps. FIG. 3C illustrates another embodiment where the edge member securing element 106 provided by the edge members 104*a* and 104*c* includes a button system. The edge member securing sub-element 106*a* may include one or more male snap button portions and the edge member securing sub-element 106*b* may include one or more corresponding female snap button portions. However, other button systems besides snap buttons may be contemplated by one skill in the art in possession of the present disclosure. FIG. 3D illustrates another embodiment where the edge member securing element 106 provided by the edge members 104*a* and 104*c* includes an extender hook system. The edge member securing sub-element 106*a* may include one or more loops positioned linear to each other and the edge member securing sub-element 106*b* may include one or more corresponding hook portions that are configured to couple with the line of loops. Additional lines of loops may be positioned along the edge member 104*a* such that a user can choose which line of loops couples to the hook portions. This allows the user to adjust the circumference of the waist aperture. While specific examples of the edge member securing elements 106 and 108 are is illustrated in FIGS. 3A-3D, one of skill in the art in possession of the present disclosure will recognize that other variations and embodiments may be contemplated and fall under the scope of the present disclosure as well.

Figure 4:
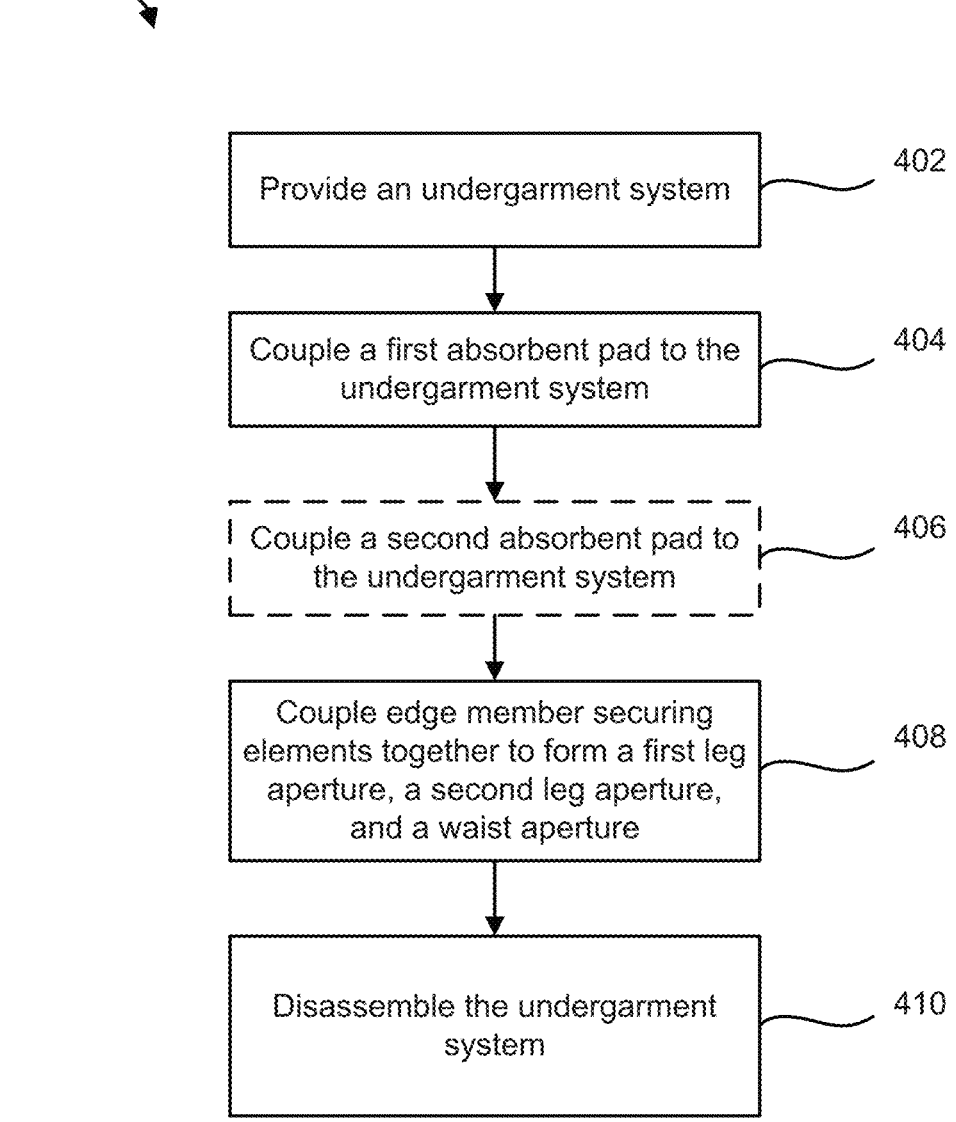
FIG. 4 illustrates a flowchart of a process of using the undergarment system and the absorbent pad of FIG. 1A-1C or 2A-2C, in accordance with some embodiments of the present disclosure.

Referring now to FIG. 4, a method 400 of assembling the undergarment system 100 of FIGS. 1A-1E and the absorbent pad 200 of FIGS. 2A-2C is illustrated. The method 400 may begin at block 402 where an undergarment system is provided. In an embodiment, at block 402, the undergarment system 100 of FIGS. 1A-1E is provided.

The method 400 may proceed to block 404 where a first absorbent pad is coupled to the undergarment system. In an embodiment, at block 404, the absorbent pad 200 may be coupled to the undergarment body portion 102 via the undergarment connector 206 and the absorbent pad connector 116 or the undergarment connector 206 alone. However, in other embodiments, the absorbent pad 200 may be inserted into the undergarment body portion cavity 114 via the pocket aperture 112. In some embodiments, block 404 may be optional as the undergarment body portion 102 may include extra layering (e.g., layer 110*b*) or the user may not desire to have the absorbent pad 200 connected to the undergarment system 100 when using the undergarment system 100.

The method 400 may then proceed to optional block 406 where a second absorbent pad is coupled to the undergarment system. In an embodiment, at block 406, a second absorbent pad 200 may be coupled to the undergarment system 100. For example, if the first absorbent pad 200 was coupled to the absorbent pad connector 116 at block 404, the second absorbent pad 200 may be inserted into the undergarment body portion cavity 114 via the pocket aperture 112. On the other hand, if the first absorbent pad 200 was inserted into the undergarment body portion cavity 114 via the pocket aperture 112 at block 404, then the second absorbent pad 200 may be coupled to the undergarment body portion 102 via the undergarment connector 206 and the absorbent pad connector 116 or the undergarment connector 206 alone. Adding the second absorbent pad 200 may allow a user to choose the level of protection the user desires without having to rely on selecting pads with varying thickness.

The method 400 may proceed to block 408 where edge member securing elements are coupled together to form a first leg aperture, a second leg aperture, and a waist aperture. In an embodiment, at block 408, the edge member securing element 106 and the edge member securing element 108 may be secured. For example, the edge member securing sub-element 106a may be coupled to edge member securing sub-element 106b. Likewise, edge member securing sub-element 108a may be coupled to edge member securing sub-element 108b. Thus, the waist aperture, the first leg aperture, and the second leg aperture are formed. Block 408 may be performed while the undergarment system 100 is in contact with the user's body such that the user is wearing the undergarment system 100 with absorbent pad(s) 200. However, the assembly of the edge member securing elements 106 and 108 may be performed while the undergarment is not on the user's body such that the user may wear the undergarment system 100 at a later time.

The method 400 may proceed to block 410 where the undergarment system is disassembled. In an embodiment, at block 410, the user may disassemble the undergarment system 100 with absorbent pad(s) 200 by decoupling the edge member securing elements 106 or 108, decoupling the absorbent pad 200 from the undergarment connector 206 from itself or the absorbent pad connector 116, or removing the absorbent pad 200 from the undergarment body portion cavity 114. While a specific method 400 is described, one of skill in the art will recognize that other modifications and alternatives may be contemplated.

Figure 5A:
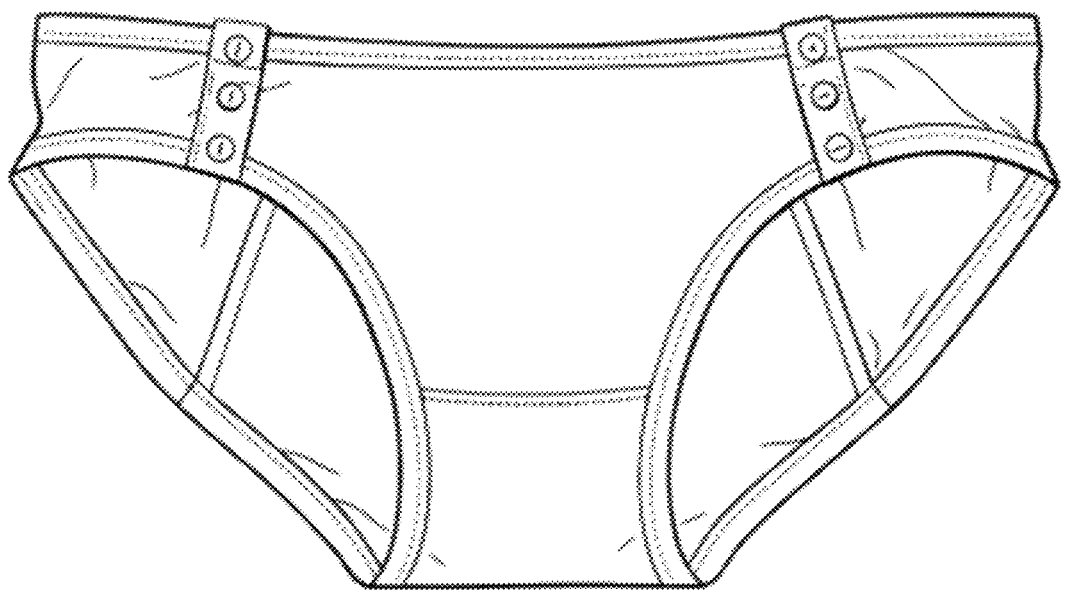
FIG. 5A illustrates an embodiment of the undergarment system of FIGS. 1A-1E, in accordance with some embodiments of the present disclosure.
Figure 5B:
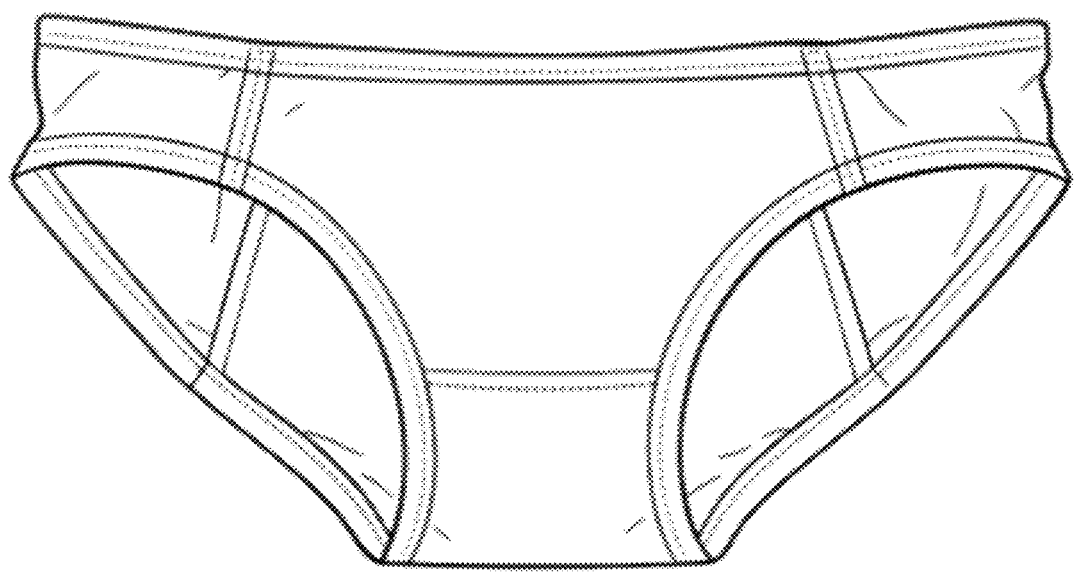
FIG. 5B illustrates an embodiment of the undergarment system of FIGS. 1A-1E, in accordance with some embodiments of the present disclosure.
Figure 5C:
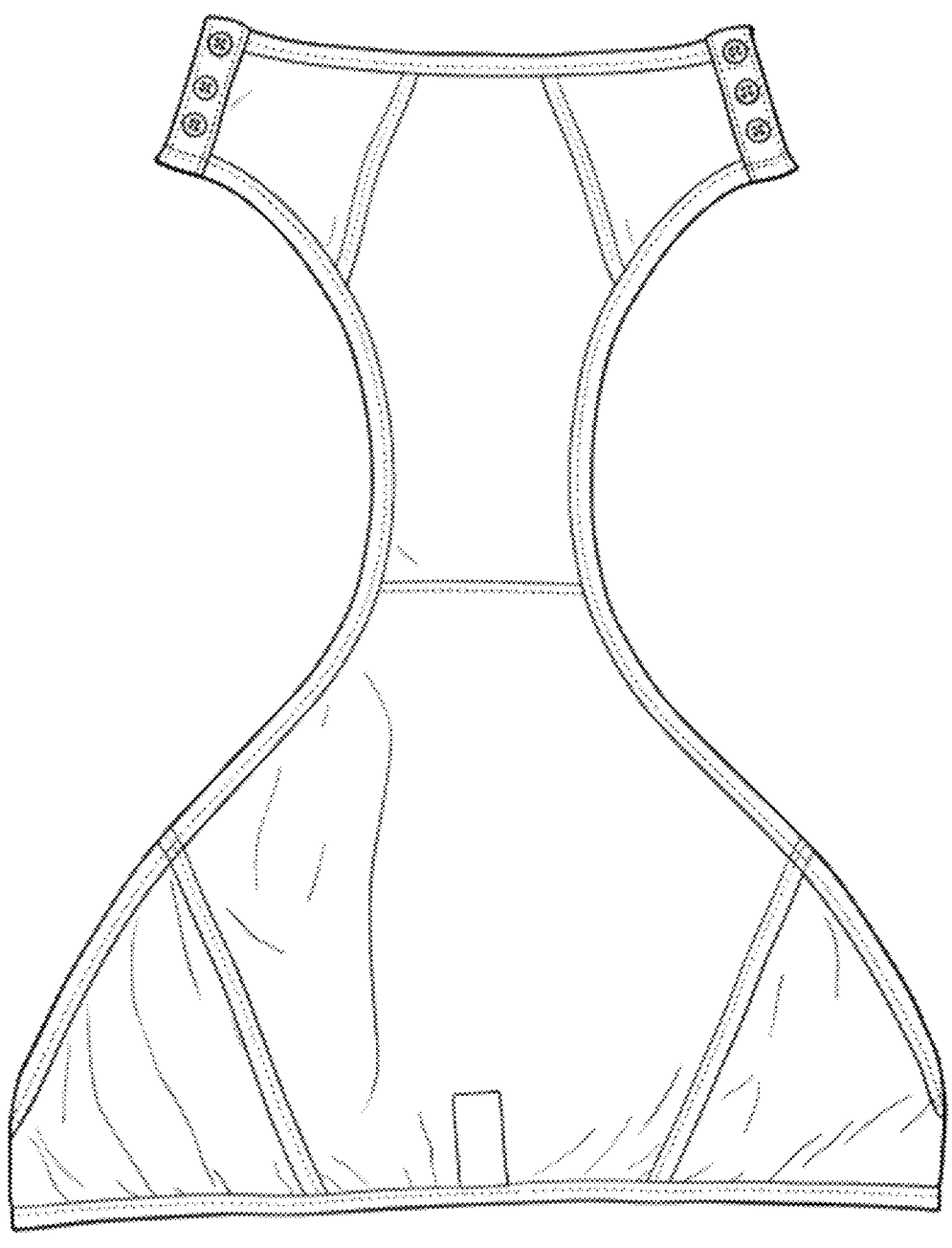
FIG. 5C illustrates an embodiment of the undergarment system of FIGS. 1A-1E, in accordance with some embodiments of the present disclosure.

FIGS. 5A, 5B, and 5C illustrate various embodiments, of the undergarment system 100 assembled and dissembled. For example, FIG. 5A illustrates the undergarment system 100 provided by a panty where the edge member securing elements 106 and 108 are provided by a button system. Similarly, FIG. 5B show the panty of FIG. 5A with alternative edge member securing elements 106 and 108 that are provided by a loop-and-hook system. FIG. 5C illustrates the panty of FIG. 5A with the edge member securing elements 106 and 108 decoupled.

Figure 6A:
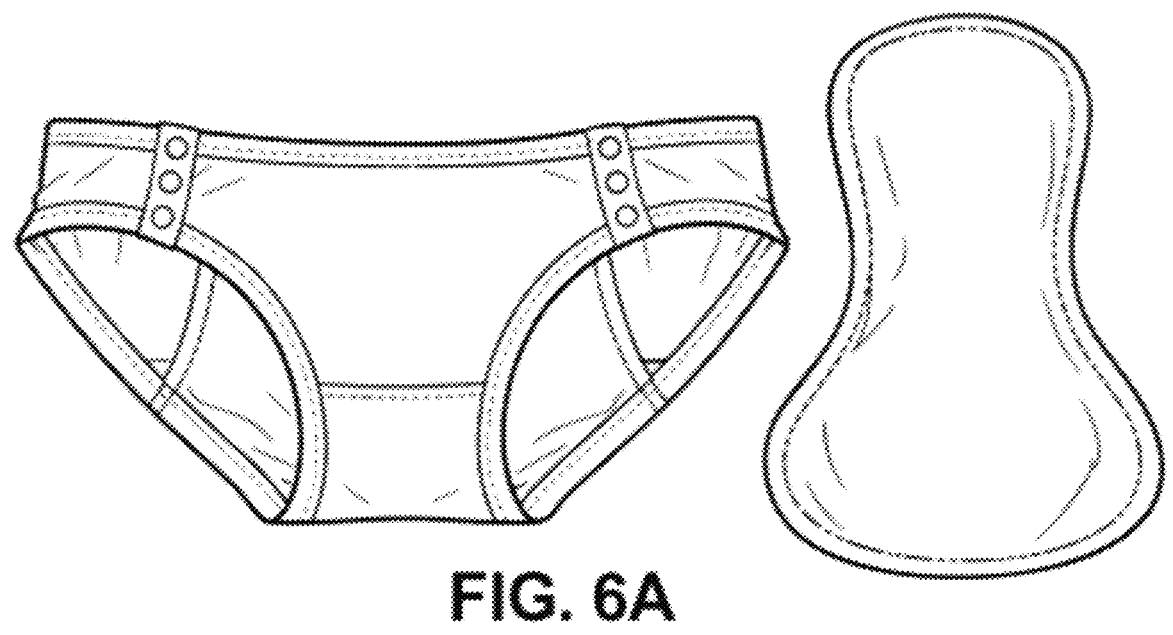
FIG. 6A illustrates an embodiment of the undergarment system of FIGS. 1A-1E with the absorbent pad of FIGS. 2A-2D, in accordance with some embodiments of the present disclosure.
Figure 6B:
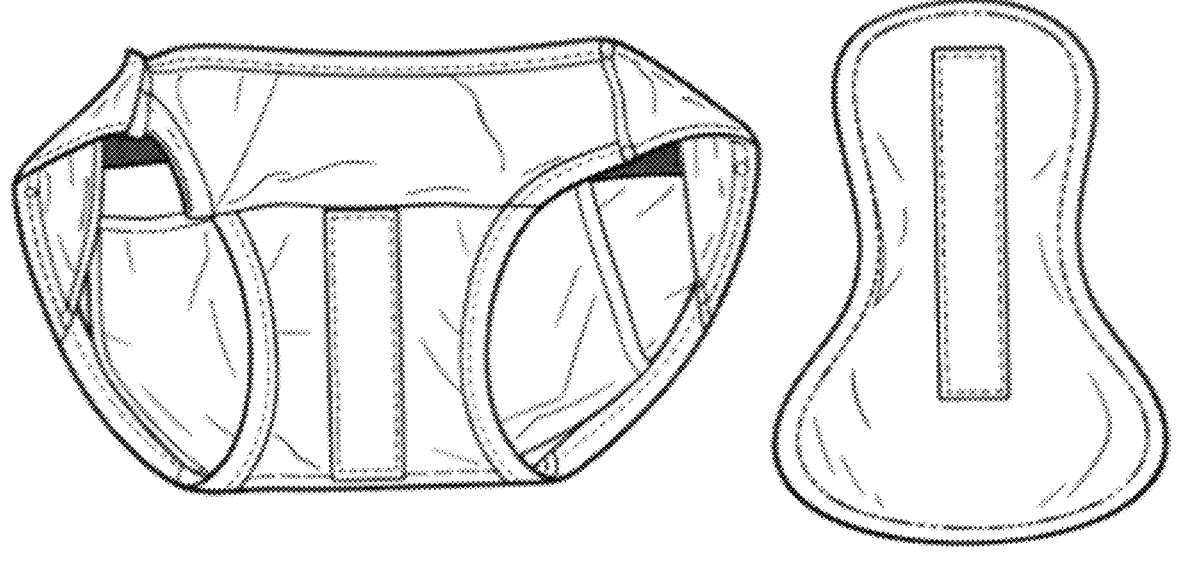
FIG. 6B illustrates an embodiment of the undergarment system of FIGS. 1A-1E with the absorbent pad of FIGS. 2A-2D, in accordance with some embodiments of the present disclosure.
Figure 7:
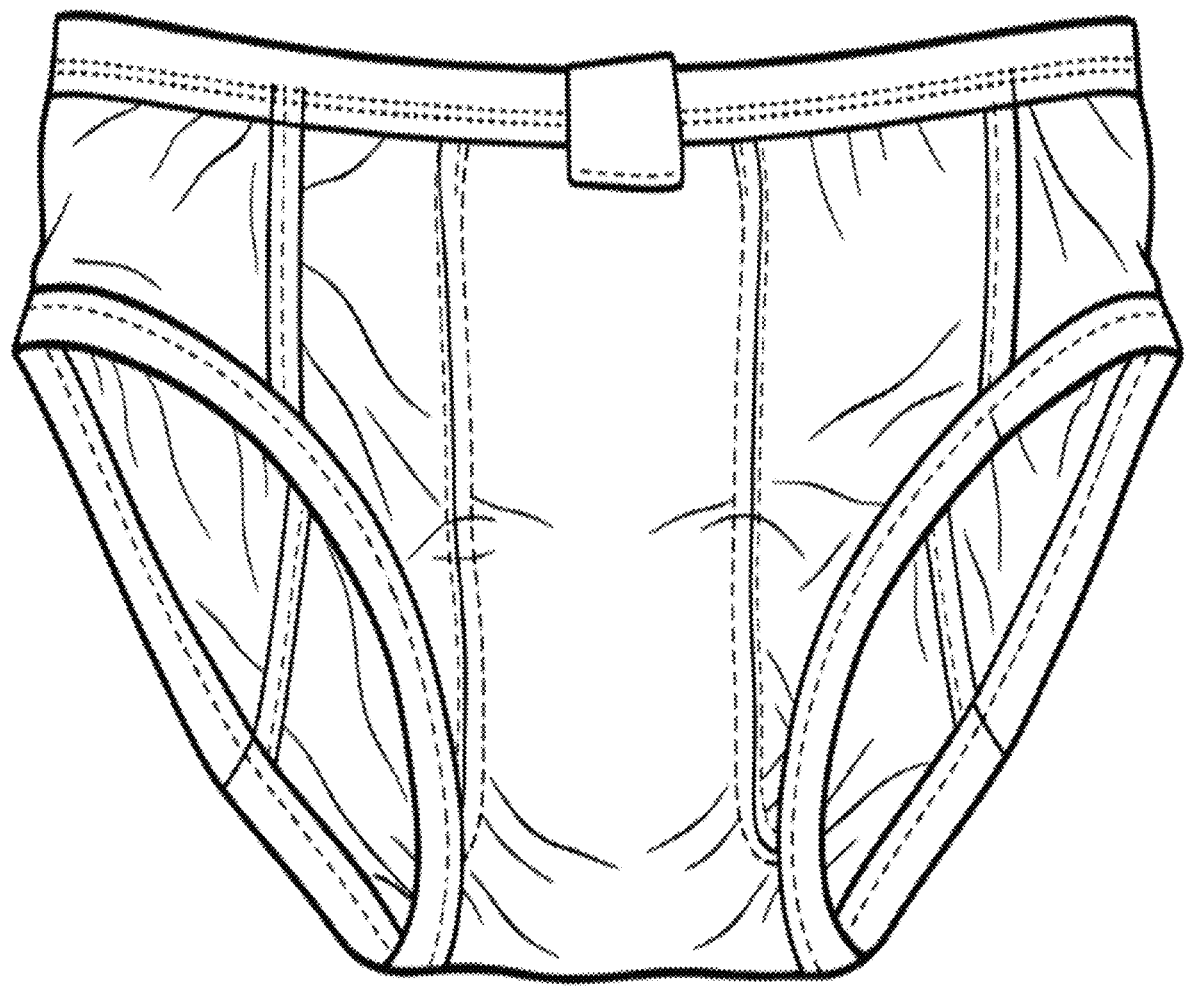
FIG. 7 illustrates an alternative embodiment of the undergarment system and undergarment body portion of FIGS. 1A-1E, in accordance with some embodiments of the present disclosure.

FIG. 6A illustrates the undergarment system 100 provided by the panty example and the absorbent pad 200. FIG. 6A illustrates an exterior of the undergarment system 100 and the absorbent pad 200 while FIG. 6B illustrates an interior of the undergarment system 100 and the absorbent pad 200 where the absorbent pad connector 116 and the undergarment connector 206 are visible. FIG. 7 illustrates the undergarment system 100 in a boxer brief configuration providing an alternatively shaped undergarment body portion 102.

Figure 8:
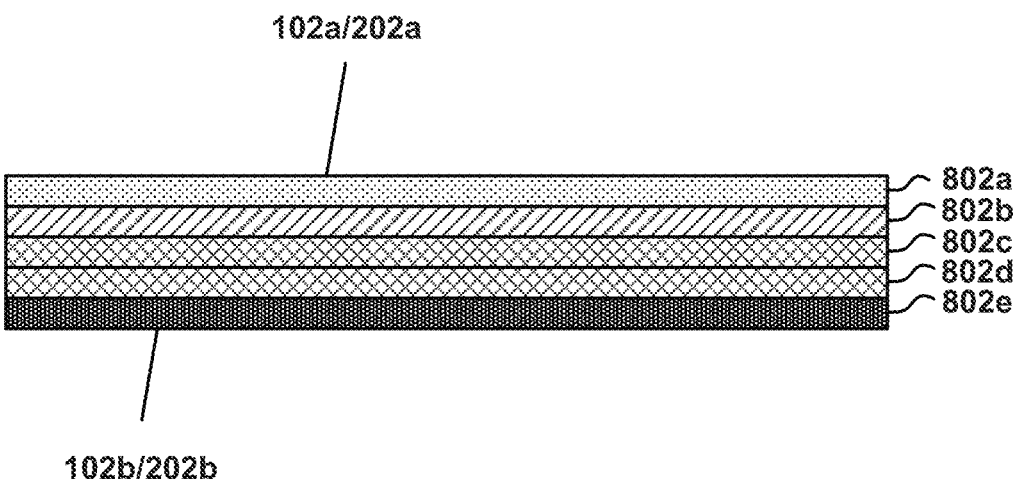
FIG. 8 illustrates a cross-sectional view of absorbent pad or the undergarment body portion, in accordance with some embodiments of the present disclosure.

FIG. 8 illustrates an alternative layering embodiment of the undergarment body portion 102 of the undergarment system 100 of FIGS. 1A-1E or the absorbent pad body portion 202 of FIGS. 2A-2C. Beginning from the undergarment body portion interior face 102a or absorbent pad body portion interior face 202a, a first layer 802a may include a material of which a portion includes bamboo fabric. In some embodiments the first layer 802a may also include spandex in addition to the bamboo fabric. For example, the first layer 802a may include a 95% bamboo and 5% spandex. However, other compositions may be contemplated (e.g., 90% bamboo and 10% spandex, 85% bamboo and 15% spandex, 80% bamboo 20% spandex or any other combination). In various embodiments, the first layer 802a may be adjacent or directly adjacent a second layer 802b. The second layer 802b may include a thermoplastic polyurethane (TPU) material for liquid proofing the body portion 102/202. In various embodiments, a third layer 802c may be adjacent the second layer 802b such that the third layer 802c is opposite the second layer 802b from the first layer 802a. The third layer 802c may include a microfiber material, which may include microfibers of nylon, polyester or other microfiber materials that would be apparent to one of skill in the art of the present disclosure. The microfiber material may be used for its absorbent or in some cases liquid repellant properties as well as for lightweight and durability. In some embodiments, an optional fourth layer 802d may be adjacent or directly adjacent the third layer 802c such that the fourth layer 802d is opposite the third layer 802c from the second layer 802b. The fourth layer 802d may include a second microfiber material that may be different than the third layer 802c or may be the same microfiber material as is included in the third layer 802c. In some embodiments, a fifth layer 802e may be included in the body portion 102/202. The fifth layer 802e may include a cotton material. For example, the fifth layer 802e may include 100% cotton. The fifth layer 802e may be adjacent or directly adjacent the fourth layer 802d such that the fifth layer 802e is opposite the fourth layer 802d from the third layer 802c. However, in some embodiments, the fifth layer 802e may replace the fourth layer 802d. The fifth layer 802e may provide the undergarment body portion exterior face 102b or absorbent pad body portion exterior face 202b. In some embodiments, a sixth layer may be directly adjacent to the first layer 802a such that the sixth layer includes the cotton material of the fifth layer 802e and provides the face 102a/202a.

Thus, systems and methods of the present disclosure provide an undergarment system that has absorption capabilities to protect the user and the user's clothing from embarrassing discharge of bodily fluids. By providing optional layering within the undergarment by attaching, detaching, inserting, or removing various absorbent pads, the user can selectively protect against body fluids. An undergarment body portion may include a pocket aperture that provides access to an undergarment body portion cavity that is configured to receive an absorbent pad. Furthermore, the absorbent pad and undergarment system may be configured to couple the absorbent pad to an undergarment body portion interior face. Furthermore, edge members of the undergarment system may include edge member securing elements that allow a user to dress or undress without moving the undergarment system up or down the user's legs.

The reader should appreciate that the present application describes several independently useful techniques. Rather than separating those techniques into multiple isolated patent applications, applicant has grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. To the extent bespoke noun phrases (and other coined terms) are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. An undergarment system, comprising: an undergarment body portion having a first edge and a second edge opposite the undergarment body portion from the first edge, wherein the undergarment body portion defines a pocket aperture and an undergarment body portion cavity; a first edge member extending from the first edge; a second edge member extending from the first edge; a third edge member extending from the second edge; and a fourth edge member extending from the second edge, wherein the undergarment body portion, the first edge member, the second edge member, the third edge member, and the fourth edge member are configured to form a waist aperture, a first leg aperture, and a second leg aperture when the first edge member is secured to the second edge member and the third edge member is secured to the fourth edge member.

2. The undergarment system of embodiment 1, wherein when the first edge member is secured to the second edge member via a first edge member securing element and the third edge member is secured to the fourth edge member via a second edge member securing element.

3. The undergarment system of embodiment 2, wherein at least one of the first edge member securing element or the second edge member securing element includes a hook and loop fastener system.

4. The undergarment system of embodiment 2, wherein at least one of the first edge member securing element or the second edge member securing element includes a button system.

5. The undergarment system of embodiment 2, wherein at least one of the first edge member securing element or the second edge member securing element includes an extender hook system.

6. The undergarment system of any one of embodiments 1-5, wherein the undergarment body portion includes a first liquid absorbent capacity that is greater than a second liquid absorbent capacity than at least one of the first edge member, the second edge member, the third edge member, or the fourth edge member.

7. The undergarment system of any one of embodiments 1-6, wherein the pocket aperture is configured to house an absorbent pad that is configured to be adjacent at least a portion of a female genital region when the undergarment system is worn by a user.

8. The undergarment system of any one of embodiments 1-7, wherein the undergarment body portion is configured to cover at least a portion of a female genital region when the undergarment system is worn by a user.

9. The undergarment system of any one of embodiments 1-8, further comprising: an absorbent pad coupled to the undergarment body portion.

10. The undergarment system of embodiment 9, wherein the absorbent pad is coupled to the undergarment body portion by being housed in the undergarment body portion cavity.

11. The undergarment system of any one of embodiments 1-10, wherein the undergarment body portion includes an absorbent pad connector.

12. The undergarment system of embodiment 11, further comprising: an absorbent pad connected to the absorbent pad connector via an undergarment connector.

13. The undergarment system of any one of embodiments 1-12, wherein at least a portion of the undergarment body portion includes: a first textile layer; a second textile layer adjacent the first textile layer, and a third textile layer opposite the first textile layer form the second textile layer, wherein the second textile layer comprises a bamboo material.

14. The undergarment system of embodiment 13, wherein the first textile layer and the second textile layer comprise a cotton material.

15. The undergarment system of any one of embodiments 1-14, further comprising: a first absorbent pad housed in the undergarment body portion cavity; a second absorbent pad that is coupled to the undergarment body portion via an undergarment connector.

16. The undergarment system of any one of embodiments 1-15, wherein the first edge member includes a means to couple the first edge member to the second edge member.

17. The undergarment system of any one of embodiments 1-16, wherein at least a portion of the undergarment body portion includes: a first textile layer; a second textile layer adjacent the first textile layer; a third textile layer opposite the first textile layer from the second textile layer; and a fourth textile layer opposite the second textile layer from the third textile layer.

18. The undergarment system of embodiment 17, wherein the first textile layer include a bamboo material and provides an undergarment body portion interior face, the second textile layer includes a thermoplastic polyurethane (TPU) material, the third textile layer includes a microfiber material, and the fourth textile layer includes a cotton material.

19. A method, comprising: providing an undergarment system that includes an undergarment body portion having a first edge and a second edge opposite the undergarment body portion from the first edge, wherein the undergarment body portion defines a pocket aperture and an undergarment body portion cavity; a first edge member extending from the first edge; a second edge member extending from the first edge; a third edge member extending from the second edge; and a fourth edge member extending from the second edge; coupling a first absorbent pad to the undergarment body portion by inserting the first absorbent pad into the undergarment body portion cavity; and coupling a second absorbent pad to the undergarment body portion via an undergarment connector provided on the second absorbent pad.

20. The method of embodiment 19, wherein the undergarment body portion, the first edge member, the second edge member, the third edge member, and the fourth edge member are configured to form a waist aperture, a first leg aperture, and a second leg aperture when the first edge member is secured to the second edge member via a first edge member securing element and the third edge member is secured to the fourth edge member via a second edge member securing element, and the method further comprises: coupling the first edge securing element and the second edge securing element to form the first leg aperture, the second leg aperture, and the waist aperture.

What is claimed is:

1. An undergarment system, comprising:

an undergarment body portion having an undergarment body portion interior face, an undergarment body portion exterior face that is located opposite the undergarment body portion from the undergarment body portion interior face, a first waist edge extending between the undergarment body portion interior face and the undergarment body portion exterior face, a second waist edge located opposite the undergarment body portion from the first waist edge and extending between the undergarment body portion interior face and the undergarment body portion exterior face, a first leg edge, and a second leg edge opposite the undergarment body portion from the first leg edge that each extend between the undergarment body portion interior face, the undergarment body portion exterior face, the first waist edge, and the second waist edge, wherein the undergarment body portion defines a pocket aperture on at least one of the first leg edge or the second leg edge and an undergarment body portion cavity;

a first edge member extending from the first leg edge;

a second edge member extending from the first leg edge;

a third edge member extending from the second leg edge; and a fourth edge member extending from the second leg edge, wherein the undergarment body portion, the first edge member, the second edge member, the third edge member, and the fourth edge member are configured to form a waist aperture, a first leg aperture, and a second leg aperture when the first edge member is secured to the second edge member and the third edge member is secured to the fourth edge member.

2. The undergarment system of claim 1, wherein when the first edge member is secured to the second edge member via a first edge member securing element and the third edge member is secured to the fourth edge member via a second edge member securing element.

3. The undergarment system of claim 2, wherein at least one of the first edge member securing element or the second edge member securing element includes a hook and loop fastener system.

4. The undergarment system of claim 2, wherein at least one of the first edge member securing element or the second edge member securing element includes a button system.

5. The undergarment system of claim 2, wherein at least one of the first edge member securing element or the second edge member securing element includes an extender hook system.

6. The undergarment system of claim 1, wherein the undergarment body portion includes a first liquid absorbent capacity that is greater than a second liquid absorbent capacity of any one of the first edge member, the second edge member, the third edge member, or the fourth edge member.

7. The undergarment system of claim 1, wherein the pocket aperture is configured to house an absorbent pad that is configured to be adjacent at least a portion of a female genital region when the undergarment system is worn by a user.

8. The undergarment system of claim 1, wherein the undergarment body portion is configured to cover at least a portion of a female genital region when the undergarment system is worn by a user.

9. The undergarment system of claim 1, further comprising:

an absorbent pad coupled to the undergarment body portion.

10. The undergarment system of claim 9, wherein the absorbent pad is coupled to the undergarment body portion by being housed in the undergarment body portion cavity.

11. The undergarment system of claim 1, wherein the undergarment body portion includes an absorbent pad connector.

12. The undergarment system of claim 11, further comprising:

an absorbent pad connected to the absorbent pad connector via an undergarment connector.

13. The undergarment system of claim 1, wherein at least a portion of the undergarment body portion includes:

a first textile layer;

a second textile layer adjacent the first textile layer, and a third textile layer opposite the first textile layer from the second textile layer, wherein the second textile layer comprises a bamboo material.

14. The undergarment system of claim 13, wherein the first textile layer and the second textile layer comprise a cotton material.

15. The undergarment system of claim 1, further comprising:

a first absorbent pad housed in the undergarment body portion cavity; and a second absorbent pad that is coupled to the undergarment body portion via an undergarment connector.

16. The undergarment system of claim 1, wherein the first edge member includes a means to couple the first edge member to the second edge member.

17. The undergarment system of claim 1 wherein at least a portion of the undergarment body portion includes:

a first textile layer;

a second textile layer adjacent the first textile layer;

a third textile layer opposite the first textile layer from the second textile layer; and a fourth textile layer opposite the second textile layer from the third textile layer.

18. The undergarment system of claim 17, wherein the first textile layer includes a bamboo material and provides an undergarment body portion interior face, the second textile layer includes a thermoplastic polyurethane (TPU) material, the third textile layer includes a microfiber material, and the fourth textile layer includes a cotton material.

19. A method, comprising:

providing an undergarment system that includes an undergarment body portion having an undergarment body portion interior face, an undergarment body portion exterior face that is located opposite the undergarment body portion from the undergarment body portion interior face, a first waist edge extending between the undergarment body portion interior face and the undergarment body portion exterior face, a second waist edge located opposite the undergarment body portion from the first waist edge and extending between the undergarment body portion interior face and the undergarment body portion exterior face, a first leg edge, and a second leg edge opposite the undergarment body portion from the first leg edge that each extend between the undergarment body portion interior face, the undergarment body portion exterior face, the first waist edge, and the second waist edge, wherein the undergarment body portion defines a pocket aperture on at least one of the first leg edge or the second leg edge and an undergarment body portion cavity;

a first edge member extending from the first leg edge;

a second edge member extending from the first leg edge;

a third edge member extending from the second leg edge; and a fourth edge member extending from the second leg edge;

coupling a first absorbent pad to the undergarment body portion by inserting the first absorbent pad into the undergarment body portion cavity; and coupling a second absorbent pad to the undergarment body portion via an undergarment connector provided on the second absorbent pad.

20. The method of claim 19, wherein the undergarment body portion, the first edge member, the second edge member, the third edge member, and the fourth edge member are configured to form a waist aperture, a first leg aperture, and a second leg aperture when the first edge member is secured to the second edge member via a first edge member securing element and the third edge member is secured to the fourth edge member via a second edge member securing element, and the method further comprises:

coupling the first edge member securing element and the second edge member securing element to form the first leg aperture, the second leg aperture, and the waist aperture.

* * * * *